US00PP08512P

United States Patent [19]

van Andel

[11] Patent Number: Plant 8,512

[45] Date of Patent: Dec. 21, 1993

[54] SPRAY CARNATION NAMED STAGITEN

[75] Inventor: Jacob van Andel, Aalsmeer, Netherlands

[73] Assignee: Van Staaveren B.V., Aalsmeer, Netherlands

[21] Appl. No.: 780,077

[22] Filed: Oct. 21, 1991

[51] Int. Cl.[5] ..... A01H 5/00

[52] U.S. Cl. ..... Plt./70.5

[58] Field of Search ..... Plt./70.2, 70.5, 70.6

*Primary Examiner*—Howard J. Locker

*Attorney, Agent, or Firm*—Tilton, Fallon, Lungmus & Chestnut

[57] ABSTRACT

A new variety of spray carnation particularly distinguished by its profuse, recurrent production of small flowers borne in a cluster the petals of which are white at the base and pink to the outer edge, the edges of which are deeply serrated and by the plant which grows rapidly in the form of a bush with abundant foliage.

1 Drawing Sheet

BACKGROUND OF THE NEW PLANT

This new spray carnation cultivar originated as a hybrid seedling developed by me at our nursery in Aalsmeer, Holland, by crossing two carnation varieties, *Dianthus superbus* and *Dianthus barbatas* (both unpatented) selected from my collection of carnations maintained for breeding purposes at Aalsmeer. The female parent of Stagiten is a plant of the species *Dianthus superbus.* The male parent is a plant of the species *Dianthus barbatus.* Stigiten is a true hybrid between *Dianthus superbus* and *Dianthus barbatus.* The present seedling was selected for propagation because of its unusual flower coloring and its sturdy, fast growing growth habit. Asexual propagation of this selected plant was done by means of cuttings under my direction at Aalsmeer. Such propagation proved to be successful and further propagation confirmed that the new variety retained all of the distinguishing characteristics of the original parent seedling and that these characteristics hold true from generation to generation and appear to be firmly fixed.

DESCRIPTION OF THE DRAWING

This new spray carnation cultivar is illustrated by the accompanying photographic drawing which, in full color, shows the distinguishing color characteristics and flower form of this plant, the color rendition being as nearly true as is reasonably possible to obtain by conventional photographic procedures.

DESCRIPTION OF THE NEW PLANT

The following is a detailed description of my new spray carnation plant with color designations according to The R.H.S. Colour Chart of The Royal Horticultural Society of London, England.

THE PLANT

Origin: Seedling.

Parentage:

*Seed parent.*—*Dianthus superbus* (unpatented).

*Pollen parent.*—*Dianthus barbatus* (unpatented).

Classification:

*Botanic.*—Dianthus hybrid.

*Commercial.*—Spray carnation.

Form: Strong erect bush having at least four stems emitted near the ground.

Height: About 60 cm.

Cane length: About 60 cm. varying with season.

Branching character: The main stem has 2–3 side branches and each side branch has 2–3 side branches.

Growth: Vigorous, upright with moderate strength.

Foliage:

*Quantity.*—Moderate.

*Number of leaves.*—16–20.

*Size of leaf.*—About 12 cm. long and 2 cm. wide.

*Shape.*—Lanceolate with straight enire margins.

*Texture.*—Smooth.

*Color.*—Upper side — RHS 137 A. Under Side — RHS 137 C.

*Ribs and veins.*—Hardly noticeable.

*Rachis.*—Hardly noticeable.

THE BUD

Size:

*Diameter.*—About 0.4 cm.

*Length.*—About 2 cm.

Form: Cylindrical.

Rate of opening: Normal.

Color:

*When sepals first divide.*—RHS 62 -A.

*When petals begin to unfurl.*—RHS 62 A/C.

Sepals.

*Number.*—Usually 5.

*Character.*—The sepals are hooded over the bud before dividing and stand up as the flower petals unfurl. The sepals are joined together at the lower part and are sharply pointed at the apex.

Calyx:

*Shape.*—Cylindrical.

*Size.*—Approximately between 0.3 and 0.4 cm. broad and between 1.5 and 2 cm. long.

*Aspect.*—Smooth.

*Splitting.*—None.

*Color.*—RHS 137 C.

Flower stem:

*Length.*—About 60 cm.

*Character.*—Erect.

*Color.*—Dark Green.

THE FLOWER

Blooming habit: Recurrent and profuse.

Flower size: Small.

*Diameter.*—About 2.5 cm.

*Depth.*—About 15. cm.

Borne: In a cluster.

Shape:

*When bloom first opens.*—Flat.

*When bloom matures.*—Flat.

Petalage:

*Number of petals.*—5.

*Arrangement.*—Imbricated.

*Form.*—Fan-shaped with deeply serrated edges.

*Texture.*—Soft.

*Appearance.*—Velvety.

*Color.*—Outer petal body — 62-C/62-A. Base — 155-D. Reverse side body — 62-D. Base — 155-D.

Fragrance: None.

Discoloration after full bloom: From RHS 62 A/C to 65 B.

Persistance: The petals hang on and dry.

Disease resistance: Good resistance to *Fusarium oxysporum* as observed at the Horticultural Experimental Station of Aalsmeer, Holland.

Lasting quality:

*On the plant.*—21 days.

*As a cut flower.*—15 days.

Changes with maturity: When the flower first opens, the color of the petal is RHS 62-A. Mature flowers have a petal color of 62-B and old flowers have a petal color of RHS 62-C.

THE REPRODUCTIVE ORGANS

Stamens:

*Number.*—5 Short, 5 long, alternated.

*Anthers.*—Size: About 1 mm. Color: Grey Green.

*Filaments.*—Length: 5 at about 0.65 cm. and 5 at about 1 cm. Color: White.

Pistils:

*Number.*—1.

*Styles.*—Length: About 1.5 cm. Color: White.

*Stigmas.*—Color: Pink.

I claim:

1. A new and distinct spray carnation plant substantially as herein shown and described, characterized by its recurrent, profuse production of small flowers which are generally white at the base and pink to the outer edge with deeply serrated edges and borne in a cluster on a fast growing, erect bush with abundant foliage.

* * * * *

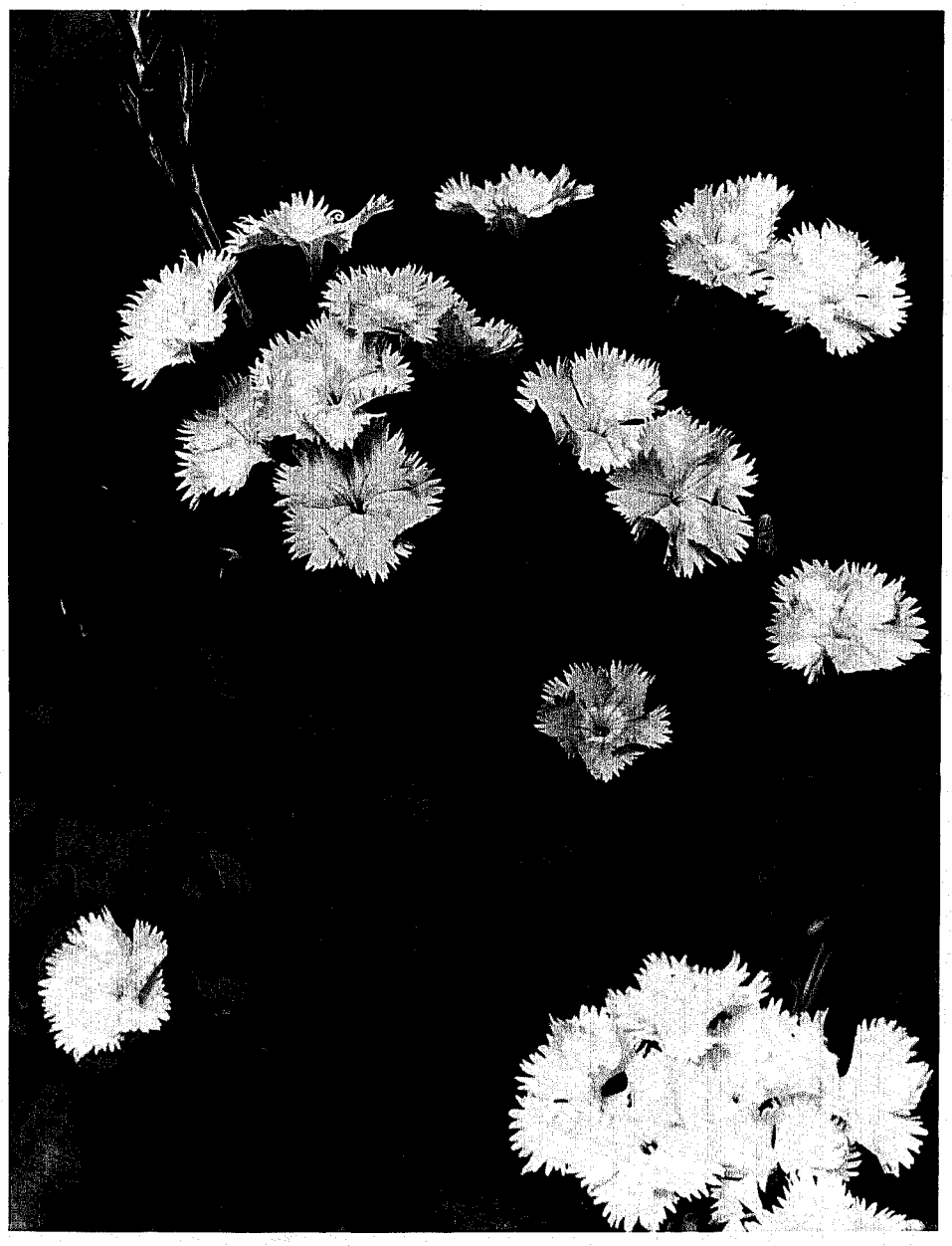

UNITED STATES PATENT AND TRADEMARK OFFICE

CERTIFICATE OF CORRECTION

PATENT NO. : Plant 8,512
DATED : December 21, 1993
INVENTOR(S) : van Andel

It is certified that error appears in the above-indentified patent and that said Letters Patent is hereby corrected as shown below:

Column 3, line 1, delete "15." and insert-- 1.5--

Signed and Sealed this

Twenty-first Day of June, 1994

*Attest:*

Bruce Lehman

BRUCE LEHMAN

*Attesting Officer*

*Commissioner of Patents and Trademarks*